United States Patent [19]

Butera

[11] 4,095,729
[45] Jun. 20, 1978

[54] FILTER PAPER DISPENSER

[76] Inventor: Anthony William Butera, 112 Tuthill St., Port Jefferson, N.Y. 11777

[21] Appl. No.: 714,951

[22] Filed: Sep. 3, 1976

[51] Int. Cl.² .............................................. B26F 3/02
[52] U.S. Cl. ........................................ 225/42; 225/47
[58] Field of Search ....................... 225/47, 40, 42, 77

[56] References Cited
U.S. PATENT DOCUMENTS

| 3,272,414 | 9/1966 | Schefer et al. ...................... 225/47 X |
| 3,489,324 | 1/1970 | Stohl ................................... 225/47 X |

Primary Examiner—Frank T. Yost

[57] ABSTRACT

This invention relates to a filter paper dispenser so designed that with ease of attachment to a Spot Smoke Tester, a ready supply of clean, indexed, and calibrated filter paper is quickly available for smoke spot testing.

1 Claim, 2 Drawing Figures

U.S. Patent  June 20, 1978  4,095,729
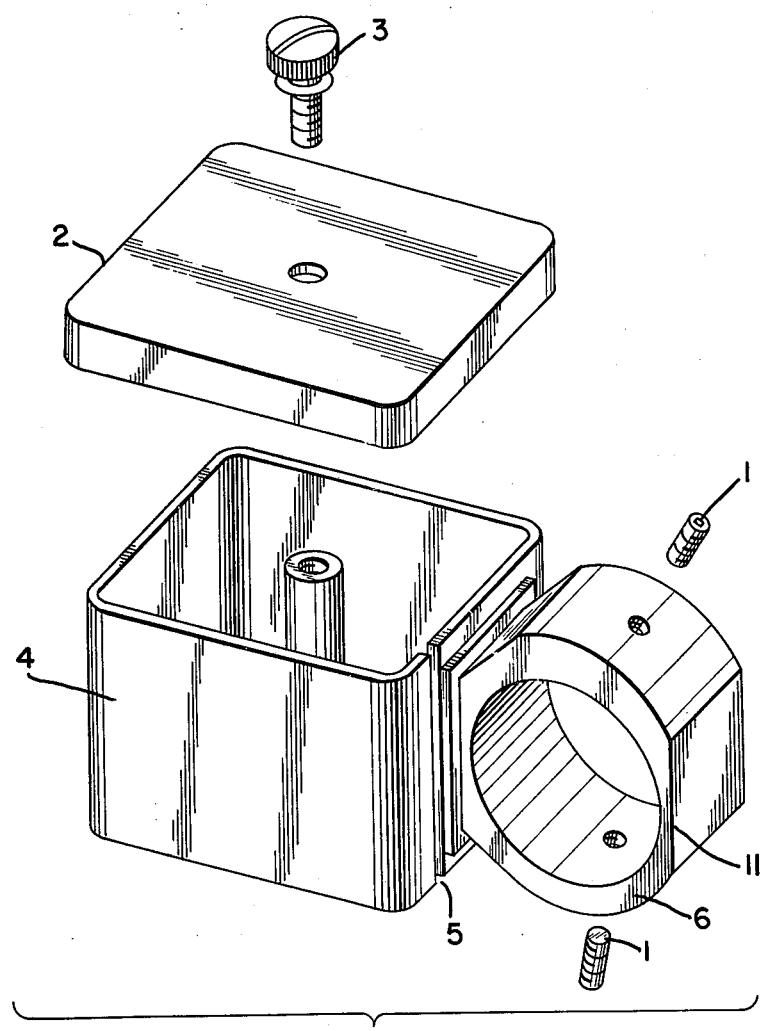
FIG. 1
FIG. 2
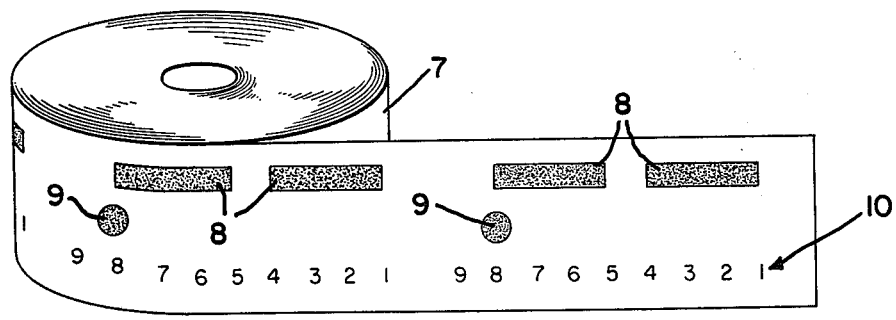

FILTER PAPER DISPENSER

BACKGROUND OF THE INVENTION

Particular difficulty has been found in the present method of spot testing the smoke content in the flu pipe of an oil burner. Namely, that the filter paper in common use today is in strip form and obtained by the technician tearing off a useable piece of paper from a serrated sheet to form a useable strip. Herein lies one of the difficulties. Usually the technician making the test has either serviced the oil burner or had made an inspection. As a result has hands are quite often covered by a quantity of soot, oil dust, and etc,. inherent with and generally found around an oil burner. Hence, the moment he selects a filter strip he imparts a print or smudge from his hands onto the filter paper even before he makes a test. This contamination can degrade the test data and lead to erroneous conclusions. Also, the concept of placing a small strip of limp paper in a narrow slot is awkward, and difficult and often falls out and onto the floor where it is further dirtied.

Another difficulty of importance is that after a spot test has been made, the test strip of filter paper must be moved or removed from the spot tested for inspection. In so doing, the test paper can be easily dropped, further contaminating the test or becoming disorientated. Since several tests are usually made on one strip a disorientation of the test strip can be confused with the first test or any other test, depending on how the paper was moved after each test.

SUMMARY OF THE INVENTION

The object of my invention is to provide an immediate supply of clean filter paper calibrated and indexed for identification. These features can be more clearly understood when considered in conjunction with the accompanied drawing.

BRIEF DESCRIPTION OF THE DRAWINGS

FIG. 1 is an exploded view of the dispenser.
FIG. 2 is a perspective view of the roll of filter paper.

DETAILED DESCRIPTION OF THE INVENTION

The dispenser is easily attatched to a standard spot tester with two set screws 1 which are pre-assembled to the support bracket 6. A one time alignment of the paper slot 5 with a standard spot smoke tester is necessary and easily achieved. The dispenser can 4 is preloaded with approximately 15 (more or less) feet of paper 7 providing a sufficient supply for many tests. The filter paper 7 is moved and handled only on the edge protruding from the spot tester, its movement being in increments as determined by the numbers on the paper 7. After a test is complete the strip can be pulled out for overall inspection and the gray density of the test spot 9 can be compared with reference repeating gray scale #8 and separated from the remainder of the roll within the container 4 by using the serrated cutting edge 11 within the container 4 by using the cutting edge 11. The advantage of the test spot 9 under an indexing number 10 is apparent as each test is ready for identification, even though the paper might be dropped or become disorentated.

Having now described my invention, I claim:

1. A dispenser for filter paper comprising a housing for enclosing a roll of strip material, the housing having two parallel end walls, two parallel side walls, a bottom portion integrally connecting said walls, and a removable top, one of said end walls having a slot running from said bottom portion to said removable top, ring like bracket means attached to said one of said end walls adjacent the slot for encircling a portion of a smoke tester, and a serrated cutting edge on said bracket means, said edge being parallel to said slot and spaced from said housing.

* * * * *